(12) United States Patent
Hendriks et al.

(10) Patent No.: US 12,285,878 B2
(45) Date of Patent: Apr. 29, 2025

(54) SKIN TREATMENT DEVICE AND METHOD OF CONTROLLING A SKIN TREATMENT DEVICE

(71) Applicant: KONINKLIJKE PHILIPS N.V., Eindhoven (NL)

(72) Inventors: Joop Hendriks, Groningen (NL); Joost Willem Frederik Nengerman, Groningen (NL); Daniele Solerio, Groningen (NL); Sachin Kumarswamy, Groningen (NL); Martijn Van Zutphen, Marum (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 391 days.

(21) Appl. No.: 17/626,834

(22) PCT Filed: Jul. 16, 2020

(86) PCT No.: PCT/EP2020/070068
§ 371 (c)(1),
(2) Date: Jan. 13, 2022

(87) PCT Pub. No.: WO2021/013662
PCT Pub. Date: Jan. 28, 2021

(65) Prior Publication Data
US 2022/0288800 A1    Sep. 15, 2022

(30) Foreign Application Priority Data
Jul. 25, 2019 (EP) .................................. 19188412

(51) Int. Cl.
B26B 21/40 (2006.01)
A61B 90/00 (2016.01)

(52) U.S. Cl.
CPC .......... B26B 21/4056 (2013.01); A61B 90/06 (2016.02); *A61B 2090/065* (2016.02)

(58) Field of Classification Search
CPC ... B26B 21/4056; B26B 19/388; B26B 19/14; A61B 90/06; A61B 2090/065; A61B 2090/0807; A46B 15/0012
See application file for complete search history.

(56) References Cited

U.S. PATENT DOCUMENTS

| 2005/0216035 A1* | 9/2005 | Kraus | ................... B26B 19/388 606/133 |
| 2009/0000126 A1 | 1/2009 | Kraus | |

(Continued)

FOREIGN PATENT DOCUMENTS

| CN | 102802465 A * | 11/2012 | ......... A46B 15/0002 |
| EP | 3092973 A1 | 11/2016 | |

(Continued)

OTHER PUBLICATIONS

International Search Report and Written Opinion Dated Aug. 13, 2020 for International Application No. PCT/EP2020/070068 Filed Jul. 16, 2020.

*Primary Examiner* — Jonathan G Riley (57) ABSTRACT

A skin treatment device provides feedback to a user relating to the force or pressure they are applying. In addition to the feedback provided for indicating that the pressure is too high, correct, or too low, there is a further feedback type when the force or pressure is below a lowest threshold value, indicating that there is no contact between the skin and the device. Providing the same feedback information when the user is applying a too low pressure as when the user has deliberately released the device from contact with the skin is thereby avoided.

18 Claims, 3 Drawing Sheets

(56) References Cited

U.S. PATENT DOCUMENTS

| | | | |
|---|---|---|---|
| 2009/0001260 A1 | 1/2009 | Klaver | |
| 2011/0276061 A1* | 11/2011 | Pfeiffer | A45D 26/0028 30/32 |
| 2013/0231618 A1* | 9/2013 | Zupkosky | B26B 21/4081 604/290 |
| 2016/0046028 A1 | 2/2016 | Meier | |
| 2016/0236360 A1 | 8/2016 | Veltman | |
| 2017/0019044 A1* | 1/2017 | Godlieb | H02P 7/29 |
| 2017/0325566 A1 | 11/2017 | Franklin | |
| 2018/0000219 A1* | 1/2018 | Roenneberg | G08B 21/182 |
| 2018/0085952 A1 | 3/2018 | Perez | |
| 2018/0085953 A1* | 3/2018 | Perez Lopez | B26B 19/48 |
| 2018/0116821 A1 | 5/2018 | Johannaber | |
| 2018/0354147 A1 | 12/2018 | Goldfarb | |
| 2018/0368549 A1* | 12/2018 | Mehaddene | A45D 26/0038 |
| 2019/0061183 A1* | 2/2019 | Neyer | B26B 19/382 |
| 2019/0121803 A1* | 4/2019 | Bertagna De Marchi | G06F 16/2379 |
| 2019/0299435 A1* | 10/2019 | Fuellgrabe | B26B 19/3886 |
| 2019/0299436 A1* | 10/2019 | Fuellgrabe | B26B 19/282 |
| 2019/0299437 A1* | 10/2019 | Fuellgrabe | B26B 19/48 |
| 2019/0306259 A1* | 10/2019 | Burghardt | B26B 21/4081 |

FOREIGN PATENT DOCUMENTS

| | | |
|---|---|---|
| EP | 3183992 A1 | 6/2017 |
| EP | 3513927 A1 | 7/2019 |
| JP | 2001128728 A | 5/2001 |
| WO | 2017/131179 A1 | 8/2017 |
| WO | 2018002755 A1 | 1/2018 |
| WO | 2018069519 A1 | 4/2018 |
| WO | 2018100155 A1 | 6/2018 |
| WO | 2019043503 A1 | 3/2019 |

* cited by examiner

SKIN TREATMENT DEVICE AND METHOD OF CONTROLLING A SKIN TREATMENT DEVICE

CROSS REFERENCE TO RELATED APPLICATIONS

This application is the U.S. National Phase application under 35 U.S.C. § 371 of International Application No. PCT/EP2020/070068 filed Jul. 16, 2020, which claims the benefit of European Patent Application Number 19188412.1 filed Jul. 25, 2019. These applications are hereby incorporated by reference herein.

FIELD OF THE INVENTION

This invention relates to skin treatment devices, such as shavers and epilators and other grooming devices. In particular, it relates to skin treatment devices which provide feedback to a user relating to their performance of the skin treatment process.

BACKGROUND OF THE INVENTION

Skin treatment, such as hair removal, typically involves application of a device, such as a shaver, against the skin.

The performance of the skin treatment device will depend on the pressure with which it is applied to the skin. It is known for example that the performance of a shaver depends on the pressure applied.

It has been proposed to provide feedback about the shaving pressure in order to guide a user to apply pressure in a range which is most optimal for the shaving process. For example, US 2016/0046028 discloses force/pressure sensing, and a warning is provided if the user is applying too much force.

It has also been proposed to use pressure sensing in order to control a skin treatment device. For example, EP 3 183 992 discloses an epilator which uses force feedback to control a drive speed of the epilator motor.

US 2018/0000219 A1 discloses an epilation device having a control unit which is able to analyze the contact pressure with which the user presses the epilation unit of the epilation device to the skin, to compare the contact pressure with at least one threshold contact pressure, and to provide feedback to the user whether the contact pressure is smaller than, equal to, or larger than the at least one threshold contact pressure. In an embodiment, the contact pressure is compared with a lower threshold, a first upper threshold and a second upper threshold. When the contact pressure is below the lower threshold, the epilation performance is too low and the user is prompted to apply more force to the epilation device. When the contact pressure is above the first threshold, the friction to the skin will cause skin irritation and the user is prompted to apply less force to the epilation device. When the contact pressure is above the second threshold, the drive unit of the epilation device may be damaged and the user is prompted to apply less force to the epilation device or the control unit may stop the drive unit.

EP 3 513 927 A1 discloses a blade razor having a sensor to measure the shaving pressure applied to the blade cartridge and an having illumination device, such as a multi-color LED, for indicating subsets of information to the user. In an embodiment, the illumination device illuminates a first color (e.g. green) when the sensor detects that the shaving pressure is optimal and a second color (e.g. yellow or red) when the sensor detects that the shaving pressure is higher than an optimal range. The notification to the user of optimal versus high or low shaving pressure sensed by the sensor may change over time based upon learning a user's preference and shaving behavior.

US 2019/0061183 A1 discloses an electric shaver comprising a sensor to detect the pressure or force with which the working head of the shaver is pressed against the skin. The shaver further comprises a control unit and a light emitter to indicate the detected pressure or force to the user. The control unit may vary the color of the emitted light depending on the detected pressure or force. For example, green light may indicate a rather low force, whereas yellow light may indicate an average force and red light may indicate a rather high force. Advantageously, the colors may be changed gradually or continuously to give precise feedback. In an embodiment, a calibration device may calibrate the relation between the color and the detected force based on the user history of the detected force. Users appreciate the provision of feedback to provide them with guidance.

However, feedback can also be a cause of annoyance if it is clearly not relevant or correct. It has been found by the inventors that the provision of unwanted feedback while a user has deliberately paused their skin treatment procedure is a particular cause of annoyance.

SUMMARY OF THE INVENTION

The invention is defined by the claims.

According to examples in accordance with an aspect of the invention, there is provided a skin treatment device, comprising:

a skin treatment head;

a force or pressure sensor for determining a force or pressure with which the skin treatment device is held against the skin of a user during use;

an output device for providing output information to the user relating to the force or pressure determined by the sensor; and a controller for controlling the output device in dependence on the force or pressure determined by the sensor, wherein the controller is adapted to control the output device to provide:

a first indication when the force or pressure determined by the sensor is in a range between a first threshold value and a second threshold value higher than the first threshold value, said first indication indicating that the force or pressure applied by the user is in a range that the user is advised to apply;

a second indication, different to the first indication, when the force or pressure determined by the sensor is above the second threshold value;

a third indication, different to the first and second indications, when the force or pressure determined by the sensor is below the first threshold value and above a third threshold value lower than the first threshold value; and a fourth indication, different to the first, second and third indications, when the force or pressure determined by the sensor is below the third threshold value and corresponds to non-contact of the skin treatment head with the skin.

The third threshold value is below a typical minimum pressure or force which arises during normal skin treatment, even for a user who applies a relatively small force. In particular, the fourth indication is provided when the force or pressure determined by the sensor corresponds to non-contact of the skin treatment head with the skin. Thus, the third threshold value is set at a sufficiently low level such that a pressure or force arising when there is no skin contact is typically below the third threshold value.

The skin treatment device provides feedback to a user about the force or pressure being applied during use, so that the user may for example be guided to apply the most appropriate force or pressure for effective use of the skin treatment device. The range of force or pressure values between the first and second threshold values corresponds to a range of force or pressure values that the user is advised to apply for optimum skin treatment results, in particular by corresponding feedback by means of the first indication.

When the force or pressure (determined by the sensor) is above the second threshold, this indicates that the pressure applied is too high. The output device then provides a different (second) indication to the user. Thus, there is real time feedback about the performance of the user in carrying out the skin treatment. When the force or pressure is below the first threshold, this indicates that the pressure applied is too low. The output device then provides a different (third) indication to the user.

In this way, the feedback system may be used to encourage the user to apply more force, less force, or maintain the same force, to optimize the effectiveness of the skin treatment.

According to the invention, there is an additional third threshold, which aims to distinguish between contact and non-contact as explained above. Below this (lowest) third threshold, there is another different (fourth) indication. Providing the same feedback information when the user is applying a too low pressure as when the user has deliberately released the device from contact with the skin is found to be annoying to the user, and undermines the trust in the user of the feedback system.

The real time force or pressure feedback may additionally be used in other ways, for example to control a motor speed as a function of the applied pressure. Alternatively, a motor drive power may be varied in dependence on the sensed pressure, in order to maintain a more constant speed despite the different motor load caused by the different pressure.

The third threshold for example is, or corresponds to, a force in a range from 0.1N to 0.5N.

This is a force threshold which intends to distinguish between contact and non-contact.

The controller may be adapted to control the output device to provide the fourth indication only when the force or pressure determined by the sensor is below the third threshold for longer than a first time threshold.

If there is a very brief interruption, for example which may arise even while the user is actively performing the skin treatment (for example, moving the skin treatment device over the contour of the body may give rise to a very brief non-contact time), the feedback (i.e. the first to third indications) is not suspended. The indication may remain in its previous state, or it may be set to the third indication while this time threshold is counted.

Brief periods of non-contact may also arise for users who generally apply a light pressure. Thus, the feedback is suspended only when the user is deliberately implementing an interruption between skin treatment periods.

The controller may be adapted to switch the skin treatment device between an active state and an inactive state, and when the force or pressure determined by the sensor is below the third threshold value, to control the output device to provide the fourth indication while maintaining the skin treatment device in the active state.

When the fourth indication is provided, the device thus remains active, so that the overall skin treatment operation is not interrupted. The provision of feedback information of no relevance is suspended, but the user can continue the skin treatment operation as soon as contact is reinstated. Thus, the device is not fully shut down. The user may for example simply be moving the skin treatment device from one part of the body (e.g. face) to another, so the device should not be shut down for this brief interruption to the skin treatment operation. This provides a more enjoyable user experience which may better encourage the user to adapt their use of the skin treatment device based on the feedback being given by the first to third indications.

The skin treatment device may further comprise a motor for driving the skin treatment head, and the controller may be adapted to actuate the motor in the active state and to stop the motor in the inactive state.

Thus, the motor remains actuated when non-contact is detected, so that the skin treatment can be resumed without delay.

The controller may be adapted to switch the skin treatment device to the inactive state if the force or pressure determined by the sensor is below the third threshold for longer than a second time threshold which is larger than the first time threshold. If there is a long interruption of contact, this suggests the user may have forgotten to turn the skin treatment device off. Thus, the contact detection may also be used to implement an auto-off function, whereby the device is switched to the inactive state, to save power.

The output device may comprise a light output device, and the first, second and third indications may each comprise a light output with respective different colors.

The user can see the light output in use, either directly or in a mirror. A simple color coding provides simple feedback for a user, e.g. red=too hard, green=OK, yellow=too soft. A blinking speed and/or a brightness may instead, or additionally, be used. Furthermore audible or tactile feedback may additionally or alternatively be used (for example for people with sight difficulties).

The fourth indication may be no light output (but optionally with the device still in the active state as explained above). Alternatively, a different type of light output may be used than is used to provide feedback (i.e. the first, second and third indications) during use. The fourth indication may be a blinking light output.

The force or pressure sensor may be arranged to measure a force or pressure mutually exerted between the skin treatment head and the skin. Alternatively, the skin treatment device further comprises a handle coupled to the skin treatment head, and the force or pressure sensor may then be arranged to measure a force or pressure mutually exerted by the handle and the skin treatment head.

The force or pressure measured may thus be an external force or pressure applied to the skin treatment device (i.e. applied to an external pressure sensor) by the skin, or an internal force or pressure which results between components of the skin treatment device. The force or pressure sensor may comprise a pair of components separated by a spring force, and a sensor for measuring the proximity of the two components, such as a magnetic sensor, for example a Hall sensor.

The output device for example comprises a light output device in the proximity of the skin treatment head. This provides an easily visible indicator, which can be seen directly or in a mirror.

The controller may be adapted to derive a performance rating in respect of a skin treatment program conducted by the user based on the force or pressure determined by the sensor during the skin treatment program.

This performance rating can be more accurate by disregarding periods of no contact, rather than considering them to be periods during which insufficient pressure has been applied.

The skin treatment device for example comprises an electric shaver, wherein the skin treatment head comprises a shaving head.

The invention also provides a method of controlling a skin treatment device, the skin treatment device comprising a skin treatment head, a force or pressure sensor for determining a force or pressure with which the skin treatment device is held against the skin of a user during use, and an output device for providing output information to the user relating to the force or pressure determined by the sensor, wherein the method comprises:

controlling the output device to provide a first indication when the force or pressure determined by the sensor is between a first threshold value and a second threshold value higher than the first threshold value, said first indication indicating that the force or pressure applied by the user is in a range that the user is advised to apply;

controlling the output device to provide a second indication, different to the first indication, when the force or pressure determined by the sensor is above the second threshold value;

controlling the output device to provide a third indication, different to the first and second indications, when the force or pressure determined by the sensor is below the first threshold value and above a third threshold value lower than the first threshold value; and controlling the output device to provide a fourth indication, different to the first, second and third indications, when the force or pressure determined by the sensor is below the third threshold value and corresponds to non-contact of the skin treatment head with the skin.

The method is preferably carried out during a non-therapeutic skin treatment such as hair cutting.

The method may comprise controlling the output device to provide the fourth indication only when the force or pressure determined by the sensor is below the third threshold for longer than a first time threshold.

The invention also provides a computer program comprising computer program code means adapted, when said program is run on a computer, to implement the method defined above.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a skin treatment device which provides feedback to a user relating to the force or pressure they are applying. In addition to feedback provided for indicating that the pressure is too high, correct, or too low, there is a further feedback type when the force or pressure is below a lowest threshold value, indicating that there is no contact between the skin and the device. Providing the same feedback information when the user is applying a too low pressure as when the user has deliberately released the device from contact with the skin is thereby avoided.

Figure 1:
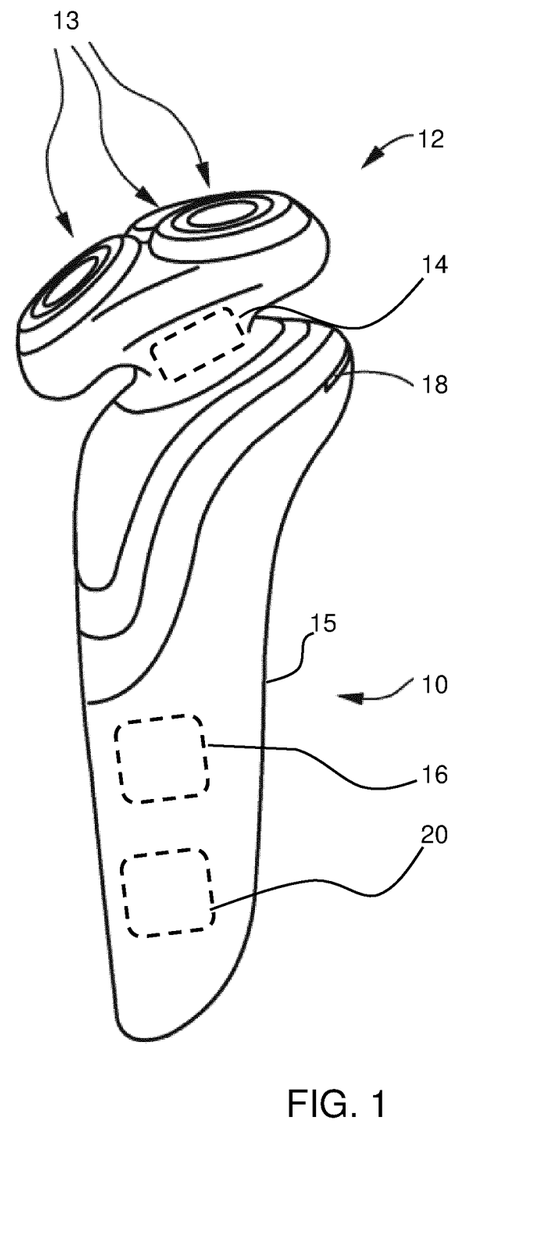
FIG. 1 shows a skin treatment device in the form of a shaver.

FIG. 1 shows a skin treatment device in the form of a shaver 10.

The shaver comprises a skin treatment head 12, namely a shaver head, and a force or pressure sensor 14 for determining a force or pressure with which the skin treatment device (in particular the head 12) is held against the skin of the user during use. The force of pressure sensor preferably has a resolution corresponding to 0.1N or better.

The operation of the device is explained with reference to a force or pressure applied. It will be understood that pressure and force may be considered to be analogous. A force or pressure sensor typically measures a force applied to a sensing area of the sensor, which thus corresponds to a particular pressure.

The shaver head in this example has three rotary shaving units 13, and they are driven by a motor 16 in the handle 15 of the shaver. The handle 15 is coupled to the treatment head 12. However, other types of shaving head are equally applicable.

An output device 18 is used to provide output information to a user relating to the pressure they are applying. This information is used to guide them in the skin treatment process, i.e. shaving in this example.

The output device 18 for example comprises one or more LEDs at an upper back region of the shaver body (near the shaving head). The LED or LEDs face outwardly in normal use of the shaver, so that they are easily seen in a shaving mirror, but the light output is preferably also directly visible. The aim is thus for the output device to be seen during use, either directly by the user or reflected in a mirror. There may be different color LEDs to provide different color outputs relating to different applied pressure. The light output may additionally or alternatively be made to flash (i.e. blink), wherein the flashing rate is indicative of the pressure applied. A brightness level may also be used as part of the feedback system.

Any other light output device may be used at any suitable location or combination of locations. Tactile feedback may also (or instead) be used. Similarly, audible feedback may also (or instead) be used.

A controller 20 is provided for controlling the output device (and the motor) in dependence on the sensed force or pressure.

The controller 20 controls the output device to generate various different indications.

A first indication (e.g. color) is provided when the force or pressure is between a first threshold value and a higher second threshold value, corresponding to a range of force or pressure values that the user is advised to apply for optimum skin treatment results. Thus, the first indication indicates that the force or pressure applied by the user is in the range for optimum skin treatment results. This tells the user they are performing the skin treatment correctly.

A second indication (different to the first indication) is used when the force or pressure is above the second threshold value. This tells the user to apply less force.

A third indication (different to the first and second indications) is used when the force or pressure is below the first threshold value and above a third threshold value, lower than the first threshold value. This tells the user to apply more force.

The third threshold value is below a typical minimum pressure or force which arises during normal skin treatment, even for a user who applies a relatively small force. In particular, the third threshold value is set at a sufficiently low level such that a pressure or force arising when there is no skin contact is typically below the third threshold value. The third threshold for example is, or corresponds to, a force in the range 0.1N to 0.5N.

A fourth indication (different to the first to third indications) is used when the force or pressure is below the third threshold value. In particular, the fourth indication is provided when the force or pressure determined by the sensor corresponds to non-contact of the skin treatment head with the skin.

There is thus real time feedback about the performance of the user in carrying out the skin treatment, in order to encourage the user to apply more force, less force, or maintain the same force, to optimize the effectiveness of the skin treatment.

By way of example only, Th1 may be 1.5N and Th2 may be 3N.

The fourth indication means that different feedback is used for the user applying a too low pressure than for the user deliberately releasing the device from contact with the skin. The fourth indication may for example be provided only when the force or pressure is below the third threshold for longer than a first time threshold.

The first time threshold is for example in the range 0.1 second to 2 seconds.

If there is a very brief interruption, for example moving shaver from one side of the face to the other, the normal feedback (i.e. the first to third indications) may still be provided.

The fourth indication may be a fourth color. It may instead be a transition from a continuous color to a flashing color. However, the fourth indication may comprise providing no output at all. However, it is not part of an auto-off function, so the device remains (preferably) immediately ready to continue the skin treatment operation once contact is reestablished.

For example, the skin treatment device may have an active state (e.g. with the motor running) and an inactive state (with the motor not running). The skin treatment device is then operated in the active state when the force or pressure is below the third threshold value. The device thus remains active, so that the overall skin treatment operation is not interrupted. The provision of feedback information of no relevance is suspended, but the user can continue the skin treatment operation as soon as contact is reestablished. This provides a more enjoyable user experience which may better encourage the user to adapt their use of the skin treatment device based on the feedback being given by the first set of indications.

The active state may instead have the motor stopped, but in a state in which it will be immediately driven when contact is detected. Thus, the force or pressure sensor remains active, and the device is not in a shut-down state.

The contact sensing implemented by the third threshold may also be used to implement a full shut down function. For example, the skin treatment device may be switched to the inactive state if the force or pressure is below the third threshold for longer than a second time threshold.

The second time threshold is for example in the range 5 seconds to 1 minute.

Figure 2:
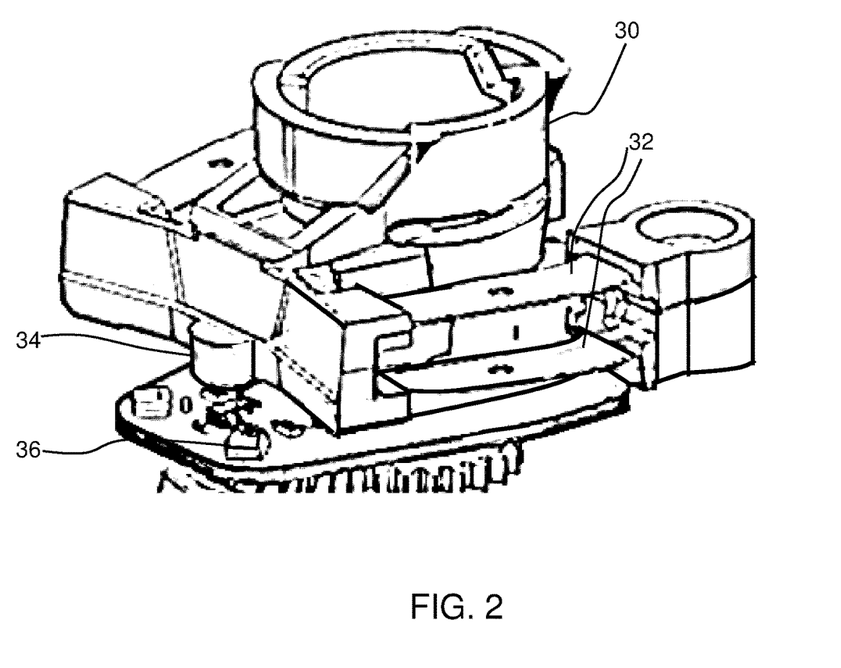
FIG. 2 shows an example of a force or pressure sensor used in the device of FIG. 1.

FIG. 2 shows one example of an implementation of the force or pressure sensor. It shows an internal part of the shaver, in the form of a support 30 to which the shaving head 12 is mounted. The support is biased away from the main body of the shaver (e.g. the handle 15) by a spring arrangement 32. Thus, the greater the force applied to the head 12 in the direction of the main body, the closer the head moves towards the body.

The distance is sensed by a magnetic sensor comprising a magnet 34 and a Hall sensor 36.

This is just one possible example of internal force sensor. The force or pressure sensor may instead be external and be contacted by the skin.

Figure 3:
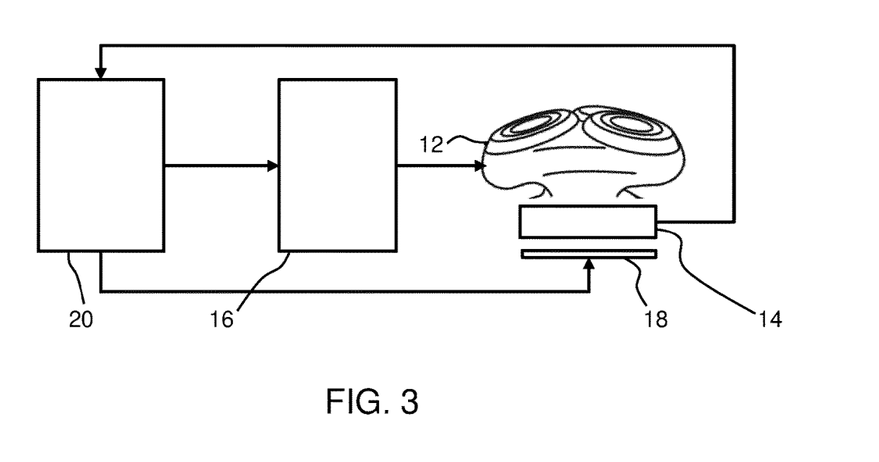
FIG. 3 shows electrical components used to implement the invention.

FIG. 3 shows electrical components used to implement the invention.

As shown, the force or pressure sensor 14 provides its output to the controller 20, and the controller controls the driving of the motor 16 as well as the output device 18.

Figure 4:
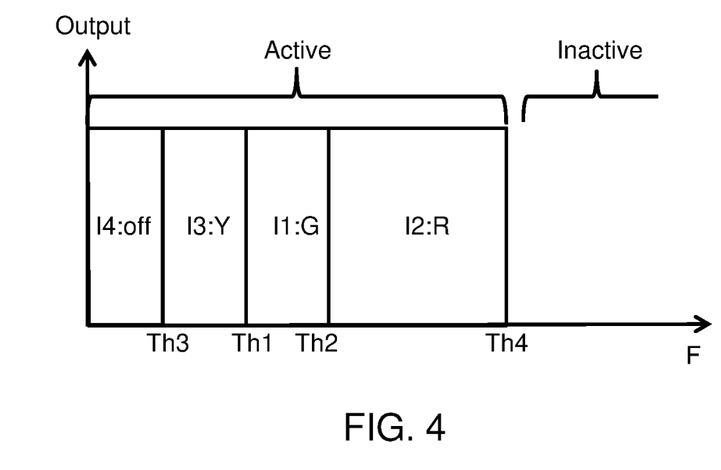
FIG. 4 shows the different outputs that may be provided in response to different sensed force or pressure.

FIG. 4 shows graphically the different outputs that may be provided in response to different sensed force or pressure.

The first indication "I1" is provided when the force or pressure determined by the sensor is between the first threshold value Th1 and the higher second threshold value Th2. This is the range for optimum skin treatment results and the output is for example a green light "G".

The second indication "I2" is used when the force or pressure is above the optimum range, and the output is for example a red light "R".

The third indication "I3" is used when the force or pressure is below the optimum range but still above the third threshold value Th3 and the output is for example a yellow light "Y".

The fourth indication "I4" is used when the force or pressure is below the third threshold value Th3 and in this example the light is off. However, the device remains "active".

FIG. 4 shows an additional (optional) threshold Th4 above which there is an auto-off function to protect the device.

In addition to providing real time feedback as explained above, the controller may derive a performance rating in respect of a skin treatment program conducted by the user based on the sensed force or pressure during and throughout the skin treatment program. For example, a percentage rating may be generated representing the time during which the optimum pressure range was achieved. This performance rating is made more accurate by disregarding periods of no contact, rather than considering them to be periods during which insufficient pressure has been applied.

Figure 5:
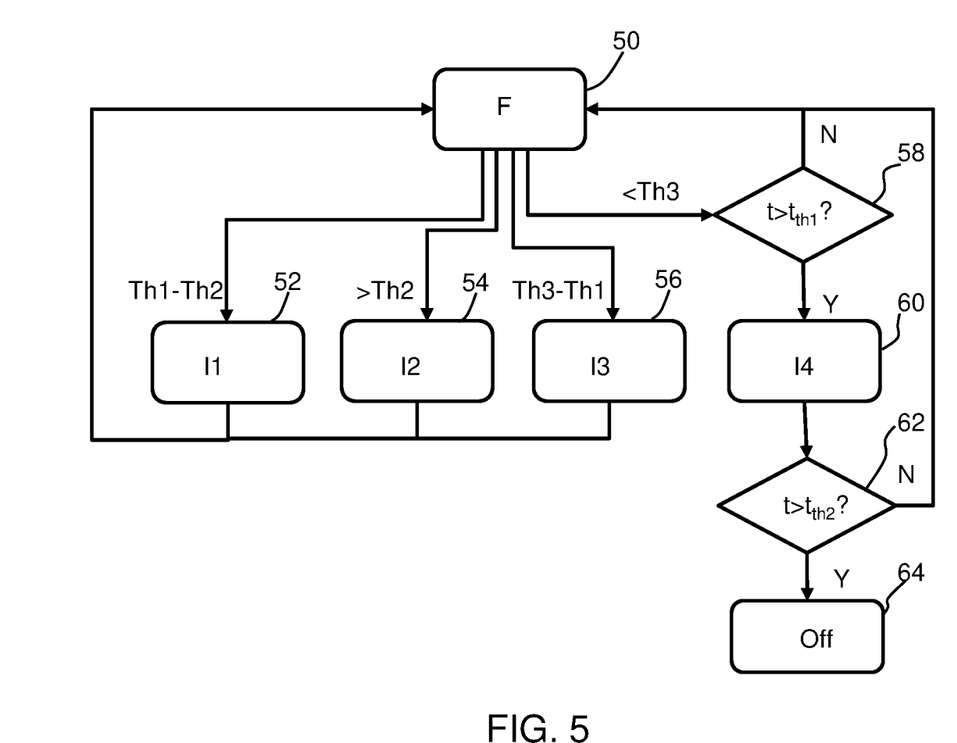
FIG. 5 shows a method of controlling a skin treatment device.

FIG. 5 shows a method of controlling the skin treatment device.

In step 50, the force or pressure is measured and is compared with the three thresholds Th1, Th2, Th3. The fourth threshold shown in FIG. 4 is not represented in the method of FIG. 5.

The first to third indications are provided in steps 52, 54 and 56.

If the force or pressure is below the third threshold, a timer is started in step 58 (during which the pressure or force continues to be monitored) to determine if the contact is released for longer than the first time threshold $t_{th1}$. During this time, the preceding feedback indication may be provided. Alternatively, the feedback may default to the third indication.

If the first time threshold is reached, the fourth indication is provided in step 60.

The timing may continue and it may then be determined in step 62 (during which the pressure or force continues to be monitored) if the non-contact lasts for the second time duration $t_{th2}$ (which could be the total non-contact time or a new timing count from the time when the fourth indication is provided). If that second time duration is reached, an auto-off function is implemented in step 64.

The feedback to the user may additionally be provided by an app, for example running on a smart phone. This applies in particular to the performance analysis rather than the real time analysis. Thus, the user may access a performance report on their mobile device after the skin treatment is concluded.

The real time force or pressure feedback may additionally be used in other ways, for example to control the motor speed as a function of the applied pressure. Alternatively, the motor drive power may be varied in dependence on the sensed pressure, in order to maintain a more constant speed despite the different motor load caused by the different pressure.

The contact sensing may also be used to provide automatic turning on of the motor when contact is sensed. When the fourth indication is provided, if the motor is kept running, it may be set to a lower motor speed, which is increased back to the required level as soon as contact is reestablished.

The invention does not only apply to mechanical shavers as described above. It may apply to shavers based on laser cutting, to epilators or to other skin treatment devices such as beard trimmers, body groomers, clippers and skin cleaning brushes. It may also apply to monitoring devices for measuring skin parameters, for example a device which captures an image of the skin while a user applies the appliance to the skin.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. The computer program may be stored/distributed on a suitable medium, such as an optical storage medium or a solid-state medium supplied together with or as part of other hardware, but may also be distributed in other forms, such as via the Internet or other wired or wireless telecommunication systems. If the term "adapted to" is used in the claims or description, it is noted the term "adapted to" is intended to be equivalent to the term "configured to". Any reference signs in the claims should not be construed as limiting the scope.

The invention claimed is:

1. A skin treatment device, comprising
   a skin treatment head;
   a force or pressure sensor for determining a force or pressure with which the skin treatment device is held against a skin of a user during use;
   an output device for providing output information to the user relating to the force or pressure determined by the sensor; and
   a controller for controlling the output device in dependence on the force or pressure determined by the sensor, wherein the controller is adapted to control the output device to provide:
   a first indication when the force or pressure determined by the sensor is in a range between a first threshold value and a second threshold value, said second threshold value being higher than the first threshold value, said first indication indicating that the force or pressure applied by the user is in a range that the user is advised to apply;
   a second indication, which is different from the first indication, when the force or pressure determined by the sensor is above the second threshold value, the second indication indicating that the force or pressure applied by the user is at any value that the user is advise is too high to apply; and
   a third indication, which is different from the first and second indications, when the force or pressure determined by the sensor is below the first threshold value and above a third threshold value, said third threshold value being lower than the first threshold value;
   a fourth audible, tactile or light indication, which is different from the first, second and third indications in response to the force or pressure determined by the sensor being below the third threshold value and corresponding to non-contact of the skin treatment head with the skin of the user.

2. The skin treatment device of claim 1, wherein the third threshold comprises a force in a range from 0.1N to 0.5N.

3. The skin treatment device of claim 1, wherein the controller is adapted to control the output device to provide the fourth indication only when the force or pressure determined by the sensor is below the third threshold for longer than a first time threshold.

4. The skin treatment device of claim 1, wherein the controller is adapted:
   to switch the skin treatment device between an active state and an inactive state; and
   when the force or pressure determined by the sensor is below the third threshold value, to control the output device to provide the fourth indication while maintaining the skin treatment device in the active state.

5. The skin treatment device of claim 4, further comprising a motor for driving the skin treatment head, wherein the controller is adapted to actuate the motor in the active state and to stop the motor in the inactive state.

6. The skin treatment device of claim 4, wherein:
   the controller is adapted to control the output device to provide the fourth indication when the force or pressure determined by the sensor is below the third threshold for longer than a first time threshold, and the controller is adapted to switch the skin treatment device to the inactive state if the force or pressure determined by the sensor is below the third threshold for longer than a second time threshold which is larger than the first time threshold.

7. The skin treatment device of claim 1, wherein the output device comprises a light output device, and the first, second and third indications each comprise a light output with respective different colors.

8. The skin treatment device of claim 1, wherein:
the force or pressure sensor is arranged to measure another force or pressure mutually exerted by the skin treatment head and the skin; or
the skin treatment device further comprises a handle coupled to the skin treatment head, and the force or pressure sensor is arranged to measure another force or pressure mutually exerted by the handle and the skin treatment head.

9. The skin treatment device of claim 1, wherein the output device comprises a light output device in the proximity of the skin treatment head.

10. The skin treatment device of claim 1, wherein the controller is adapted to derive a performance rating in respect of a skin treatment program conducted by the user based on the force or pressure determined by the sensor during the skin treatment program.

11. The skin treatment device of claim 1, wherein the skin treatment head comprises a shaving head configured for use with a shaver.

12. A method of controlling a skin treatment device, the skin treatment device comprising a skin treatment head, a force or pressure sensor for determining a force or pressure with which the skin treatment device is held against the skin of a user during use, and an output device for providing output information to the user relating to the force or pressure determined by the sensor, wherein the method comprises:
controlling the output device to provide a first indication when the force or pressure determined by the sensor is between a first threshold value and a second threshold value, said second threshold value being higher than the first threshold value, said first indication indicating that the force or pressure applied by the user is in a range that the user is advised to apply;
controlling the output device to provide a second indication, which is different from the first indication, when the force or pressure determined by the sensor is above the second threshold value, the second indication indicating that the force or pressure applied by the user is at any value that the user is advised is too high to apply; and
controlling the output device to provide a third indication, which is different from the first and second indications, when the force or pressure determined by the sensor is below the first threshold value and above a third threshold value, said third threshold value being lower than the first threshold value;
controlling the output device to provide a fourth audible, tactile or light indication, which is different from the first, second and third indications, in response to the force or pressure determined by the sensor being below the third threshold value and corresponding to non-contact of the skin treatment head with the skin of the user.

13. The method of claim 12, further comprising:
controlling the output device to provide the fourth indication only when the force or pressure determined by the sensor is below the third threshold for longer than a time threshold.

14. The method of claim 12, wherein the method is performed using a non-transitory, computer-readable medium having computer-executable instructions on a computing device.

15. The method of claim 12, further comprising:
switching the skin treatment device between an active state and an inactive state; and
when the force or pressure determined by the sensor is below the third threshold value, controlling the output device to provide the fourth indication while maintaining the skin treatment device in the active state.

16. The method of claim 15, further comprising:
actuating a motor in the active state;
driving the skin treatment head; and
stopping the motor in the inactive state.

17. The method of claim 15, further comprising:
controlling the output device to provide the fourth indication when the force or pressure determined by the sensor is below the third threshold for longer than a first time threshold, and
switching the skin treatment device to the inactive state if the force or pressure determined by the sensor is below the third threshold for longer than a second time threshold which is larger than the first time threshold.

18. The method of claim 12, further comprising:
deriving a performance rating in respect of a skin treatment program conducted by the user based on the force or pressure determined by the sensor during the skin treatment program.

* * * * *